US00PP17338P2

(12) United States Plant Patent
Maloy

(10) Patent No.: US PP17,338 P2
(45) Date of Patent: Jan. 2, 2007

(54) ***PITCAIRNIA* PLANT NAMED 'RED DRAGON'**

(50) Latin Name: *Pitcairnia hitchcockiana*
Varietal Denomination: Red Dragon

(75) Inventor: Andrew David Maloy, Waitakere (NZ)

(73) Assignee: Malbec Partnership, Auckland (NZ)

( * ) Notice: Subject to any disclaimer, the term of this patent is extended or adjusted under 35 U.S.C. 154(b) by 0 days.

(21) Appl. No.: 11/146,223

(22) Filed: Jun. 6, 2005

(51) Int. Cl.
*A01H 5/00* (2006.01)

(52) U.S. Cl. ..... Plt./370
(58) Field of Classification Search ..... Plt./370
See application file for complete search history.

(56) References Cited

PUBLICATIONS

Upov Plant Variety Database UPOV–ROM 2006/01 search for cultivar Red Dragon.*

* cited by examiner

*Primary Examiner*—Kent Bell
*Assistant Examiner*—Annette H Para
(74) *Attorney, Agent, or Firm*—C. A. Whealy

(57) ABSTRACT

A new and distinct cultivar of *Pitcairnia* plant named 'Red Dragon', characterized by its upright plant habit with outwardly arching leaves; mostly straight scapes with long and upright inflorescences with numerous flowers; conspicuous bright red-colored flower bracts; and long-lasting inflorescences.

1 Drawing Sheet

Botanical designation: *Pitcairnia hitchcockiana.*
Cultivar denomination: 'Red Dragon'.

BACKGROUND OF THE INVENTION

The present Invention relates to a new and distinct cultivar of *Pitcairna* plant, botanically known as *Pitcairnia hitchcockiana,* and hereinafter referred to by the cultivar name 'Red Dragon'.

The new *Pitcairnia* is a product of a planned breeding program conducted by the Inventor in Auckland, New Zealand. The objective of the breeding program is to develop new *Pitcairnias* with relatively straight scapes with long inflorescences and numerous flowers.

The new *Pitcairnia* originated from a cross-pollination made by the Inventor in 1999 of two unnamed proprietary seedling selections of *Pitcairnia hitchcockiana*, not patented. The cultivar Red Dragon was discovered and selected by the Inventor as a flowering plant within the progeny of the cross-pollination in a controlled environment in Auckland, New Zealand in January, 2001.

Asexual reproduction of the new cultivar by divisions in Auckland, New Zealand has shown that the unique features of this new *Pitcairnia* are stable and reproduced true to type in successive generations.

SUMMARY OF THE INVENTION

Plants of the cultivar Red Dragon have not been observed under all possible environmental conditions. The phenotype may vary somewhat with variations in environment and culture such as temperature and light intensity without, however, any variance in genotype.

The following traits have been repeatedly observed and are determined to be the unique characteristics of 'Red Dragon'. These characteristics in combination distinguish 'Red Dragon' as a new and distinct cultivar of *Pitcairnia:*

1. Upright plant habit with outwardly arching leaves.
2. Mostly straight scapes with long and upright inflorescences with numerous flowers.
3. Conspicuous bright red-colored flower bracts.
4. Long-lasting inflorescences.

Plants of the new *Pitcairnia* can be compared to plants of the parent selections. In side-by-side comparisons conducted by the Inventor in Auckland, New Zealand, plants of the new *Pitcairnia* differ from plants of the parent selections in the following characteristics:

1. Plants of the new *Pitcairnia* had straighter scapes than plants of the parent selections.
2. Plants of the new *Pitcairnia* had longer inflorescences with more flowers per inflorescence than plants of the parent selections.
3. Plants of the new *Pitcairnia* had darker-colored flower bracts than plants of the parent selections.

Plants of the new *Pitcairnia* differ from *Pitcairnia* cultivars known to the Inventor in the following characteristics:

1. Plants of the new *Pitcairnia* had straighter scapes than plants of *Pitcairnia* cultivars known to the Inventor.
2. Plants of the new *Pitcairnia* had longer inflorescences with more flowers per inflorescence than plants of *Pitcairnia* cultivars known to the Inventor.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Pitcairnia.*

The photograph at the top of the sheet is a close-up view of a typical inflorescence of 'Red Dragon'.

The photograph at the bottom of the sheet comprises a side perspective view of a typical flowering plant of 'Red Dragon' grown in a container.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and the following description were grown in 15-cm containers in a non-shaded double polyethylene-covered greenhouse in Auckland, New Zealand. During the production of the plants, day temperatures ranged from 10 to 30° C. and night temperatures ranged from 5 to 15° C. Plants were about three years old when the photographs and description were taken.

Botanical classification: *Pitcairnia hitchcockiana* cultivar Red Dragon.

Parentage: Cross-pollination of two unnamed proprietary seedling selections of *Pitcairnia hitchcockiana*, not patented.

Propagation:

*Type.*—By divisions.

*Time to initiate roots.*—About one to two months.

*Root description.*—Fibrous, fine; light brown in color.

*Rooting habit.*—Freely branching; dense.

Plant description:

*Form.*—Upright plant habit with outwardly arching leaves and mostly straight scapes with long and upright inflorescences with numerous flowers and conspicuous flower bracts.

*Plant height.*—About 40 to 90 cm.

*Plant diameter.*—About 60 to 90 cm.

*Vigor.*—Moderately vigorous.

*Foliage description.*—Arrangement/appearance: Rosette, simple; outwardly arching. Length: About 40 to 55 cm. Width: About 2.5 to 3.3 cm. Shape: Linear. Apex: Sharply acute. Base: Clasping. Margin: Entire. Texture, upper and lower surfaces: Smooth, glabrous; leathery. Venation pattern: Parallel. Color: Developing leaves, upper surface: 146A. Developing leaves, lower surface: 146B. Fully developed leaves, upper surface: 137A. Fully developed leaves, lower surface: 146B. Veins, upper and lower surfaces: Slightly lighter than lamina.

Inflorescence description:

*Inflorescence form.*—Mostly straight scapes with long, upright and non-branching inflorescences; numerous flowers subtended by conspicuous imbricate flower bracts.

*Quantity of inflorescences per plant.*—Typically five inflorescences develop per year.

*Inflorescence longevity.*—Inflorescences of the new *Pitcairnia* are very long-lasting; on the plant, inflorescences last about 60 to 100 days; as a cut flower, inflorescences last about two to four weeks. Flowers persistent.

*Natural flowering season and time to flower.*—Plants flower from the spring through the fall in New Zealand.

*Fragrance.*—None detected.

*Inflorescence length.*—Relatively long, about 15 to 22 cm.

*Inflorescence diameter.*—About 5 to 6.5 cm.

*Quantity of flowers per inflorescence.*—Numerous, about 50 to 60.

*Flowers.*—Corolla: Arrangement: Three petals, gameopetalous; imbricate. Length: About 4.8 to 5.5 cm. Width: About 5.5 mm. Shape: Linear. Apex: Sharply acute. Base: Clasping. Margin: Entire. Texture, inner and outer surfaces: Smooth, glabrous; membranous. Color, inner and outer surfaces: Towards the apex, 187A; mid-section, 187B; towards the base and margins, 155B. Calyx: Arrangement: Three sepals, gameosepalous; imbricate. Length: About 2.1 cm. Width: About 5 mm. Shape: Linear. Apex: Sharply acute. Base: Clasping. Margin: Entire. Texture, inner and outer surfaces: Smooth, glabrous; membranous. Color, inner surface: 155B; towards the apex, 45A; apex color becoming closer to 155B with development. Color, outer surface: 155A; towards the apex, 45D; apex color becoming closer to 155A with development.

*Reproductive organs.*—Stamens: Quantity per flower: Six. Anther length: About 8.5 mm. Anther color: Close to 14B. Pollen: Abundant. Pollen color: 14A. Pistils: Quantity per flower: One. Pistil length: About 4 cm. Style length: About 2 to 2.5 cm. Style color: 155B. Ovary: Superior with three locules. Ovary color: 155B.

*Seeds.*—Length: About 2 mm. Diameter: Less than 0.5 mm. Color: 162A to 162B.

*Flower bracts.*—Arrangement: Arranged spirally along the main axis. Quantity per inflorescence: About 50 to 60; one per flower. Length: About 7.5 cm. Width: About 1 to 3 cm. Shape: Ensiform. Apex: Apiculate; recurving. Base: Clasping. Margin: Entire. Texture, upper and lower surfaces: Smooth, glabrous; waxy. Color: When developing, inner surface: Towards the apex, 187A fading to 46A; towards the base, 155A; margins, 46B. When developing, outer surface: Towards the apex, 187A fading to 46B; towards the base, 155A. Fully opened, inner and outer surfaces: Towards the apex, 187A; mid-section and base, 46A.

*Scape description.*—Length: About 60 cm. Diameter: About 5 to 10 mm. Aspect: Mostly straight. Strength: Strong. Texture: Smooth. Color: 150C to 150D occasionally overlain with 45D.

*Scape bracts.*—Arrangement: Arranged spirally along the main axis. Quantity per inflorescence: About 50 to 60. Shape: Ensiform. Apex: Apiculate; recurving. Base: Clasping. Margin: Entire. Texture, upper and lower surfaces: Smooth, glabrous; waxy. Length: About 7.5 cm. Width: About 1 to 3 cm. Texture, upper and lower surfaces: Smooth, glabrous; waxy. Color: When developing, inner surface: Towards the apex, 187A fading to 46A; mid-section and base, 155A; margins, 46B. When developing, outer surface: Towards the apex, 187A fading to 46B; mid-section and base, 155A. Fully developed, inner and outer surfaces: Towards the apex, 187A; mid-section and base, 46A.

Temperature tolerance: Plants of the new *Pitcairnia* have been observed to tolerate temperatures from about 1 to 35° C.

Disease pest resistance: Plants of the new *Pitcairnia* have not been observed to resistant to pathogens and pests common to *Pitcairnia*.

It is claimed:

1. A new and distinct cultivar of *Pitcairnia* plant named 'Red Dragon', illustrated and described.

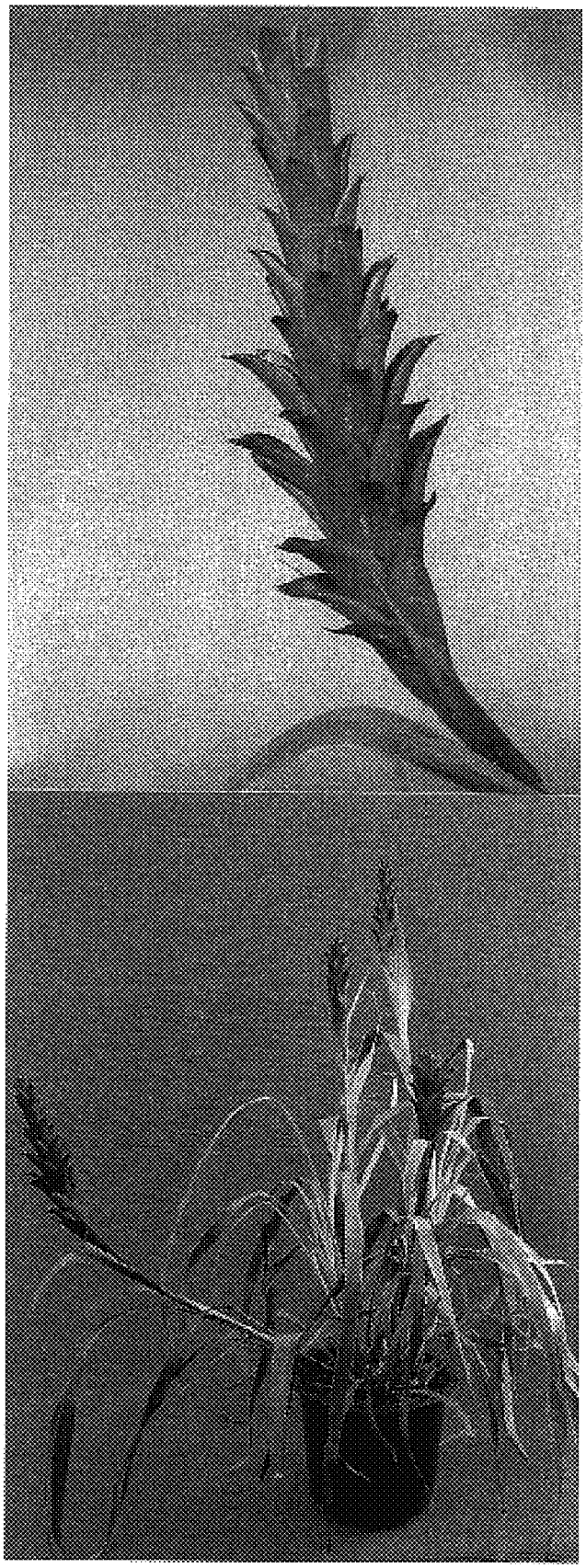

* * * * *